US012350469B2

United States Patent
Jazayeri et al.

(10) Patent No.: US 12,350,469 B2
(45) Date of Patent: *Jul. 8, 2025

(54) IMPACT TESTING APPARATUSES AND METHODS FOR DRUG DELIVERY DEVICES

(71) Applicant: AMGEN INC., Thousand Oaks, CA (US)

(72) Inventors: Julian Jazayeri, Woodland Hills, CA (US); Sean Fitzgibbon, Camarillo, CA (US); Joshua Tamsky, Thousand Oaks, CA (US); Christopher R. Folk, San Diego, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/588,264

(22) Filed: Feb. 27, 2024

(65) Prior Publication Data

US 2024/0197996 A1 Jun. 20, 2024

Related U.S. Application Data

(63) Continuation of application No. 18/071,861, filed on Nov. 30, 2022, now Pat. No. 11,938,304, which is a
(Continued)

(51) Int. Cl.
*A61M 5/20* (2006.01)
*A61M 5/142* (2006.01)
*G01L 5/00* (2006.01)

(52) U.S. Cl.
CPC ......... *A61M 5/2033* (2013.01); *G01L 5/0052* (2013.01); *A61M 2005/14288* (2013.01); *A61M 2205/332* (2013.01); *A61M 2205/3331* (2013.01)

(58) Field of Classification Search
CPC ...... A61M 5/2033; A61M 2005/14288; A61M 2205/332; A61M 2205/3331; G01L 5/0052
See application file for complete search history.

(56) References Cited

U.S. PATENT DOCUMENTS

| 11,200,298 B2 | 12/2021 | Fitzgibbon et al. |
| 2002/0123716 A1* | 9/2002 | VanDiver ............ A61M 5/1452 604/65 |

(Continued)

FOREIGN PATENT DOCUMENTS

| CN | 103118737 A * | 5/2013 | ............ A61M 37/00 |
| GB | 2311866 A | 10/1997 | |

(Continued)

OTHER PUBLICATIONS

CN-103118737-A, English translation (Year: 2013).*
(Continued)

*Primary Examiner* — Ryan D Walsh
(74) *Attorney, Agent, or Firm* — MARSHALL, GERSTEIN & BORUN LLP

(57) ABSTRACT

Impact testing apparatuses are disclosed which simulate and measure various impact-related events associated with the operation of a drug delivery device. The impact testing apparatus may include an impactor configured to simulate a plunger rod of the drug delivery device, and a guide sleeve configured to receive a syringe corresponding to the drug delivery device. The syringe may have a proximal end, a distal end defining an outlet, and an interior chamber extending between the proximal and distal ends and carrying a plunger. Additionally, the impact testing apparatus may include an energy source configured to reduce a distance between the impactor and the plunger so that the impactor strikes the plunger. Various sensors may be included to measure characteristics of one or more impacts caused by
(Continued)

the impactor. Methods of impact testing a syringe filled with a fluid and carrying a plunger are also disclosed.

21 Claims, 9 Drawing Sheets

Related U.S. Application Data continuation of application No. 16/306,379, filed as application No. PCT/US2017/031544 on May 8, 2017, now Pat. No. 11,541,176.

(60) Provisional application No. 62/345,608, filed on Jun. 3, 2016.

(56) References Cited

U.S. PATENT DOCUMENTS

| | | |
|---|---|---|
| 2004/0231667 A1 | 11/2004 | Horton et al. |
| 2009/0188311 A1 | 7/2009 | Cadieux et al. |
| 2015/0328405 A1 | 11/2015 | Metzner et al. |

FOREIGN PATENT DOCUMENTS

| | | |
|---|---|---|
| WO | WO-0154566 A1 | 8/2001 |
| WO | WO-2006067480 A1 | 6/2006 |
| WO | WO-2006116997 A1 | 11/2006 |
| WO | WO-2014059240 A1 | 4/2014 |
| WO | WO-2017008960 A1 | 1/2017 |
| WO | WO-2020091981 A1 | 5/2020 |
| WO | WO-2020169824 A1 | 8/2020 |

OTHER PUBLICATIONS

International Search Report and Written Opinion for International Application No. PCT/US2017/031544, dated Aug. 3, 2017.
European Patent Application No. 17723913.4, Communication Pursuant to Article 94(3) EPC, dated Jan. 13, 2022.
Non-final Office Action, U.S. Appl. No. 16/306,379 mailed Mar. 23, 2022.
Syringe Testing Video by ADMET Testing Systems—https://www.youtube.com/watch?v=q7-QHPRAfcs&t=59s (Uploaded Jan. 29, 2010) (Year: 2010).
Testing Syringe Plunger Actuation Force—Mecmesin Force Measurement by Mecmesin—https://www.youtube.com/watch?v=4mkyO49OA2E (Uploaded Apr. 4, 2013) (Year: 2013).
Non-final Office Action, U.S. Appl. No. 18/071,861, mailed Jul. 21, 2023.

* cited by examiner

IMPACT TESTING APPARATUSES AND METHODS FOR DRUG DELIVERY DEVICES

CROSS-REFERENCE TO RELATED APPLICATIONS

This is a continuation of U.S. patent application Ser. No. 18/071,861, filed Nov. 30, 2022, which is a continuation of U.S. patent application Ser. No. 16/306,379, filed Nov. 30, 2018, which is the U.S. National Phase of International Patent Application No. PCT/US2017/031544, filed May 8, 2017, which is an application claiming the benefit of priority of U.S. Provisional Patent Application No. 62/345,608, filed Jun. 3, 2016. The entire contents of each of the foregoing are incorporated herein by reference for all purposes.

FIELD OF THE DISCLOSURE

The present disclosure generally relates to impact testing and, more particularly, to simulating and measuring characteristics of one of more impacts caused by the operation of a drug delivery device.

BACKGROUND

Automated injector devices for drug delivery, including autoinjectors and on-body injectors, have grown in popularity in recent years. These devices offer several benefits, including simplicity of use as compared with traditional methods of delivery such as manually-operated syringes.

Injector devices typically include a drive mechanism (e.g., a spring) that operates on a syringe in response to a triggering event such as the patient pressing a button. The drive mechanism may cause a needle to be inserted into the patient and/or drive a plunger to discharge the drug through the needle.

Damage to the syringe and/or drug may occur if the drive mechanism exerts an excessive load on the plunger. The barrel of the syringe is particularly susceptible to damage as it is usually made of glass. Furthermore, an excessive load may be felt and/or heard by the patient in the form of a "slap" or "bump," which may distract or disturb the patient and thus result in incomplete drug delivery.

Drive mechanisms tend to apply excessive loads for various reasons. For instance, the force provided by the drive mechanism may decrease as the plunger is advanced. Spring-type drive mechanisms oftentimes suffer from this problem, because of the inverse relationship existing between the length of a spring and its applied force. As a result, providing sufficient energy for drug delivery at the end of a plunger stroke may require the drive mechanism to release an excessive amount of energy at the beginning of the plunger stroke.

Further, the growth in treatments requiring high viscosity drugs such as biologics has resulted in the need for more powerful drive mechanisms. Because kinetic energy is proportional to velocity squared, even an incremental increase in the velocity at which the drive mechanism operates can result in a large change in the net kinetic energy applied to the syringe or drug. In general, it is difficult to predict whether the syringe or drug will be damaged, because of the multiple components involved with drug delivery.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings are necessarily to scale.

FIG. 3 is a perspective cutaway view of a mounting assembly used by the impact testing apparatus of FIG. 2a.

Same reference numerals are used in the drawings to identify same or similar elements and structures in the various embodiments.

SUMMARY

Figure 1A:
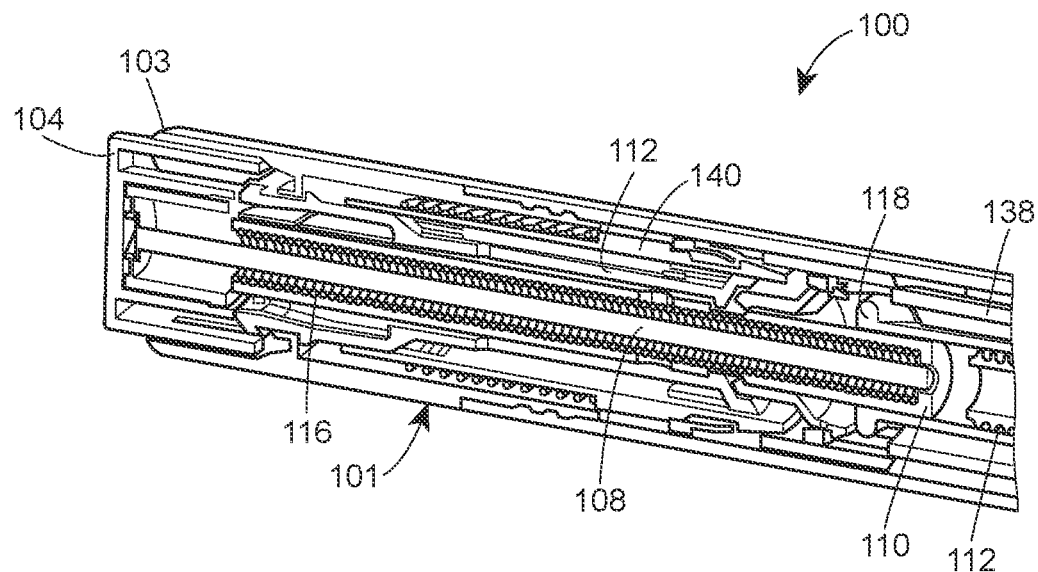
FIG. 1A illustrates a cutaway view of a proximal end of one autoinjector whose operation can be simulated by the impact testing apparatuses and methods of the present disclosure.

One aspect of the present disclosure provides a testing apparatus for simulating and measuring characteristics of one or more impacts experienced during operation of a drug delivery device. The testing apparatus may include a guide sleeve, an impactor, an energy source, and a monitoring system. The guide sleeve may be configured to receive a syringe, wherein the syringe has a proximal end, a distal end defining an outlet, and an interior chamber extending between the proximal and distal ends and carrying a plunger. The impactor may be configured to simulate a plunger rod of the drug delivery device. The energy source may be configured to reduce a distance between the impactor and the plunger such that the impactor strikes the plunger. The monitoring system may include at least one of: (a) a pressure sensor configured to output a pressure signal representative of a pressure of a fluid expelled from the outlet of the syringe, or (b) a first load cell configured to output a first force signal representative of one or more impacts caused by the impactor.

Another aspect of the present disclosure provides a testing apparatus for simulating and measuring characteristics of an impact experienced during operation of a drug delivery device. The testing apparatus may include a guide sleeve, an impactor, an energy source, an anvil member, and a first load cell. The guide sleeve may be configured to receive a syringe, wherein the syringe has a proximal end, a distal end defining an outlet, and an interior chamber extending between the proximal and distal ends and carrying a plunger. The impactor may be configured to simulate a plunger rod of the drug delivery device. The anvil member may support the syringe and may be configured to hold the syringe stationary relative to the impactor when the impactor strikes the plunger.

Yet another aspect of the present disclosure provides a method of impact testing a syringe filled with a fluid and carrying a plunger. The method may include: (a) inserting the syringe into a guide sleeve; (b) activating an energy source to cause an impactor to strike the plunger; and (c) measuring at least one characteristic of at least one impact caused by the impactor.

DETAILED DESCRIPTION

Generally, the present disclosure relates to impact testing apparatuses and methods which simulate various operations of a drug delivery device, such as an autoinjector or an on-body injector, and which measure characteristics of those operations. Such characteristics include, but are not limited to, force(s) applied to one or more internal components by a drive mechanism of the drug delivery device, fluid pressure(s) of a drug expelled from the drug delivery device, and velocitie(s) of one or more driven components of the drug delivery device. The impact testing apparatus may be configured to simulate, under normal and/or accelerated conditions, one or more impacts occurring during the operation of a drug delivery device, including an impact that occurs when a plunger rod strikes a plunger and/or an impact that occurs when a syringe or a syringe carrier strikes an interior wall of the drug delivery device. By providing empirical data on impact events, the testing apparatuses and methods may facilitate the design and manufacture of drug delivery devices which are less likely to experience component failure (e.g., syringe barrel fractures) and less likely to cause damage to the drug product itself.

Figure 1B:
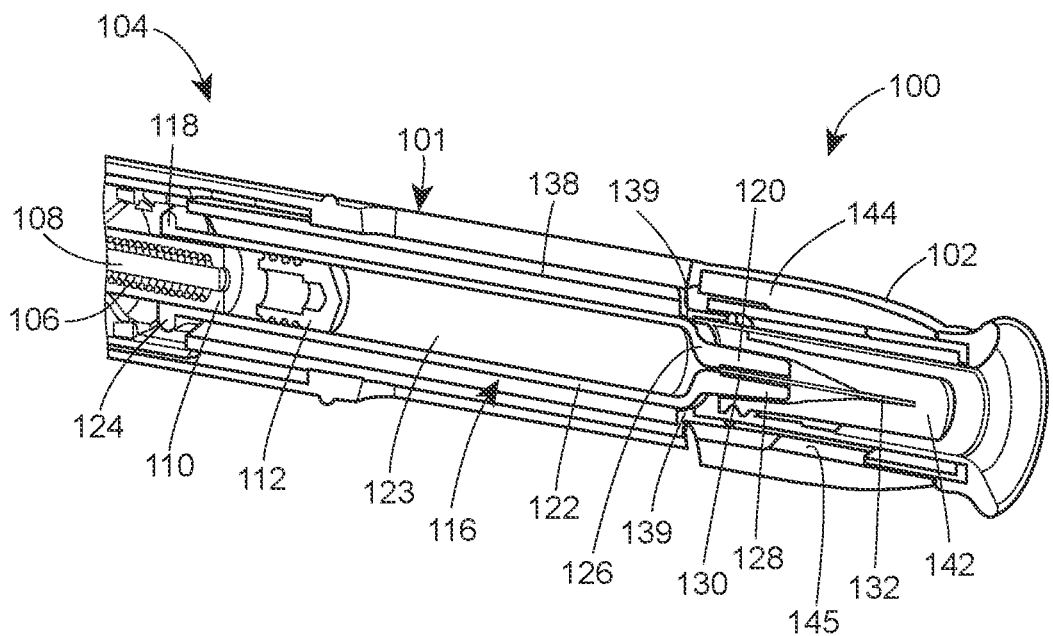
FIG. 1B depicts a cutaway view of a distal end of the autoinjector of FIG. 1A.

Before describing details of the impact testing apparatuses and methods of the present disclosure, described below with reference to FIGS. 1A and 1B is an example autoinjector firing sequence. This discussion provides context for the types of impact-related events which can be simulated and measured by the impact testing apparatuses and methods disclosed herein. It is noted, however, that the techniques of the present disclosure are not limited to autoinjectors and may be applied to other drug delivery devices, including, for example, on-body injectors.

FIGS. 1A and 1B illustrate an example autoinjector 100 having a proximal end 102 and a distal end 104. The operation of the autoinjector 100 can be simulated, in at least some respects, by the impact testing apparatuses and methods described below. The autoinjector 100 represents only one type of autoinjector which can be simulated by the impact testing apparatuses and methods of the present disclosure. As an alternative example, the impact testing apparatuses and methods can be used to simulate an autoinjector that, unlike the autoinjector 100, does not include automatic needle insertion. Generally, the impact testing apparatuses and methods of the present disclosure can be configured to simulate any drug delivery device having a drive mechanism that exerts a load on a syringe or other element for the purpose of delivering a drug to a patient, as well as other drug delivery devices not specifically mentioned herein.

Various implementations and configurations of the autoinjector 100 are possible. In at least one embodiment, the autoinjector 100 may be configured as a pen-type autoinjector. Furthermore, the autoinjector 100 may be configured as a disposable device for delivering a single dose of a drug, or as a reusable device capable of delivering multiple doses of a drug. In some embodiments, the autoinjector 100 may be pre-loaded with a pre-filled syringe; whereas, in other embodiments, the end user or patient may be responsible for loading the autoinjector 100 with the syringe, which may or may not be pre-filled.

Referring to FIG. 1A, the autoinjector 100 may include a shell or housing 101, which may be open at the distal end 102 and closed at the proximal end 103. The housing 101 may be constructed as a single, unitary component or constructed from multiple components or sections that are combined into a single, integral unit. The housing 101 can be made of plastic or any other suitably rigid material. An actuator 104 (e.g., a button) may protrude from the proximal end 103 of the housing 101 and may be depressible into the housing 101 by a user to activate the autoinjector 100.

A spring 106, which functions as an energy source, may be disposed along a spring guide rod 108 inside a plunger rod 110. Collectively, the components 106-110 may be referred to as a "drive mechanism," as these components store, and release during operation, kinetic energy used by the autoinjector 100. In an energized state, as shown in FIG. 1A, the spring 106 may be compressed within plunger rod 110. When the actuator 104 is depressed, it may de-couple an actuator sleeve 112 from the plunger rod 110, thereby allowing the spring 106 to expand and move the plunger rod 110 in a distal direction. In turn, the plunger rod 110 may strike and displace a plunger-stopper (or simply a "plunger") 112 which is positioned along a same axis as the plunger rod 110.

Looking to FIG. 1B, the autoinjector 100 may further include a syringe 116 having a proximal end 118, a distal end 120, and a barrel 122 extending between the proximal end 118 and the distal end 120. The proximal end 118 of the syringe 116 may include an annular flange 124. The distal end 120 of syringe 116 may include a shoulder 126 which narrows into a cone-shaped member 128. An outlet 130 may extend through the cone-shaped member 128 to provide fluid communication between an interior chamber 123 of the barrel 122 and a needle 132 attached to the cone-shaped member 128. The plunger 112 may be movably disposed in the barrel 120 and configured to slide along an interior wall of the barrel 120 while maintaining a seal. Movement of the plunger 112 toward the distal end 120 of the syringe 116 may advance a fluid column (e.g., a drug) toward a shoulder 126, then into the outlet 130, and finally out through the needle 132.

With continued reference to FIG. 1B, at least a portion of the syringe 116 may be encased within a syringe carrier 138. In some embodiments, the syringe carrier 138 may be fixedly connected to the syringe 116, such that the two components move together as a single unit during operation. The syringe carrier 138 may interface with a syringe driver 140 carried by the plunger rod 110. Movement of the plunger 110 in the distal direction may cause the syringe driver 140 to move the syringe carrier 138 and the syringe 116 in the distal direction. Furthermore, the syringe carrier 138 may include a shoulder 139 at its distal end which generally conforms to the contour of the shoulder 126 of the syringe 116, thereby enabling the syringe carrier 138 to grip the distal end 120 of the syringe 116.

A needle shield 142 may removably enclose both the cone-shaped member 128 of the syringe 116 and the needle 132 prior to activation of the autoinjector 100. Before its removal, the needle shield 142 may be contained within a front shell 144, which may constitute the distal end 102 of the housing 101. By removing the needle shield 142, it is possible for the needle 132 to be moved by the syringe driver 140 in the distal direction to pierce the patient's skin. To limit the extension of the needle 132 from the housing 101, an interior wall 145 of the front shell 144 may provide an internal stop that limits travel of the syringe carrier 138 in the distal direction. This may be accomplished by the interior wall 145 having a passage which narrows towards the distal end of the front shell 144 and/or by the inclusion of an inwardly protruding annular ridge (not illustrated) which catches and holds the shoulder 139 of the moving syringe carrier 138.

In use, the patient may remove the needle shield 142, place the autoinjector 100 against his or her skin, and then depress the actuator 104 or otherwise initiate operation of the autoinjector 100. As mentioned above, depressing the actuator 104 may release the energy of the compressed spring 106. In response, the spring 106 may expand and drive the plunger rod 110 in the distal direction, which in turn advances the plunger 112 and the syringe carrier 138 in the distal direction.

Two impact events may occur as a result of distal movement of the plunger rod 110. The first impact may occur when the moving plunger rod 110 strikes the stationary plunger 112. The second impact may occur when the moving syringe carrier 138 strikes the stationary front shell 144. The forces of these two impacts have to potential to break the glass or other material used to construct the barrel 122.

More particularly, when the plunger rod 110 strikes the plunger 112, a first impact load may be generated. In turn, the first impact load may generate a first pressure wave that propagates through the fluid column. For the combination of materials and geometries typical of glass syringes, this pressure wave may "couple" to the glass barrel 122 as it propagates axially. This coupling may result in a reduction of wave speed and radial motion of the barrel 122. Furthermore, the coupled wave may oscillate through the syringe 116.

After the plunger rod 110 impacts the plunger 112, the plunger rod 110, the syringe 116, and the syringe carrier 138 may advance together in the distal direction. This motion inserts the needle 132 into the patient's skin. The second impact load is generated when the syringe carrier 138 impacts the internal stop defined by the front shell 144. The second impact load produces a second pressure wave that radiates through some or all of the same components as the first pressure wave. In some embodiments, the plunger rod 110 strike against the plunger 112 and the syringe carrier 138 strike against the front shell 144 may produce similar pressure waves. These pressure waves result in localized stresses, which even in low occurrences may result in fracturing of the glass barrel 122.

In some embodiments, the entire firing sequence, including both the first and second impacts, may take only several millisecond to complete. Also, while operation of the present embodiment of the autoinjector 100 involves the plunger rod 110 impacting the plunger 112 before the syringe carrier 138 impacts the front shell 144, in alternative embodiments, this sequence of impacts may be reversed. However, for the purposes of discussion, an impact event corresponding to the plunger rod 110 striking the plunger 112 is referred to herein as the "first impact," and an impact event corresponding to the syringe carrier 138 striking an internal wall of the housing 101 is referred to herein as a "second impact."

Referring now to FIGS. 2-5, illustrated is a schematic representation of one embodiment of an impact testing apparatus 200 according to principles of the present disclosure. Generally, the impact testing apparatus 200 is capable of simulating two different impact events caused by the operation of a drug delivery device (e.g., the first and second impacts described above). Further, the impact testing apparatus 200 is capable of measuring and evaluating one or more characteristics of each impact event including, but not limited to, force, pressure, and/or velocity. While the impact events simulated by the impact testing apparatus 200 may be similar to those experienced during operation of the autoinjector 100, the impact testing apparatus 200 is not limited to simulating autoinjector-related impact events, and can be configured to simulate impact events associated with other types of drug delivery devices including on-body injectors.

Figure 2A:
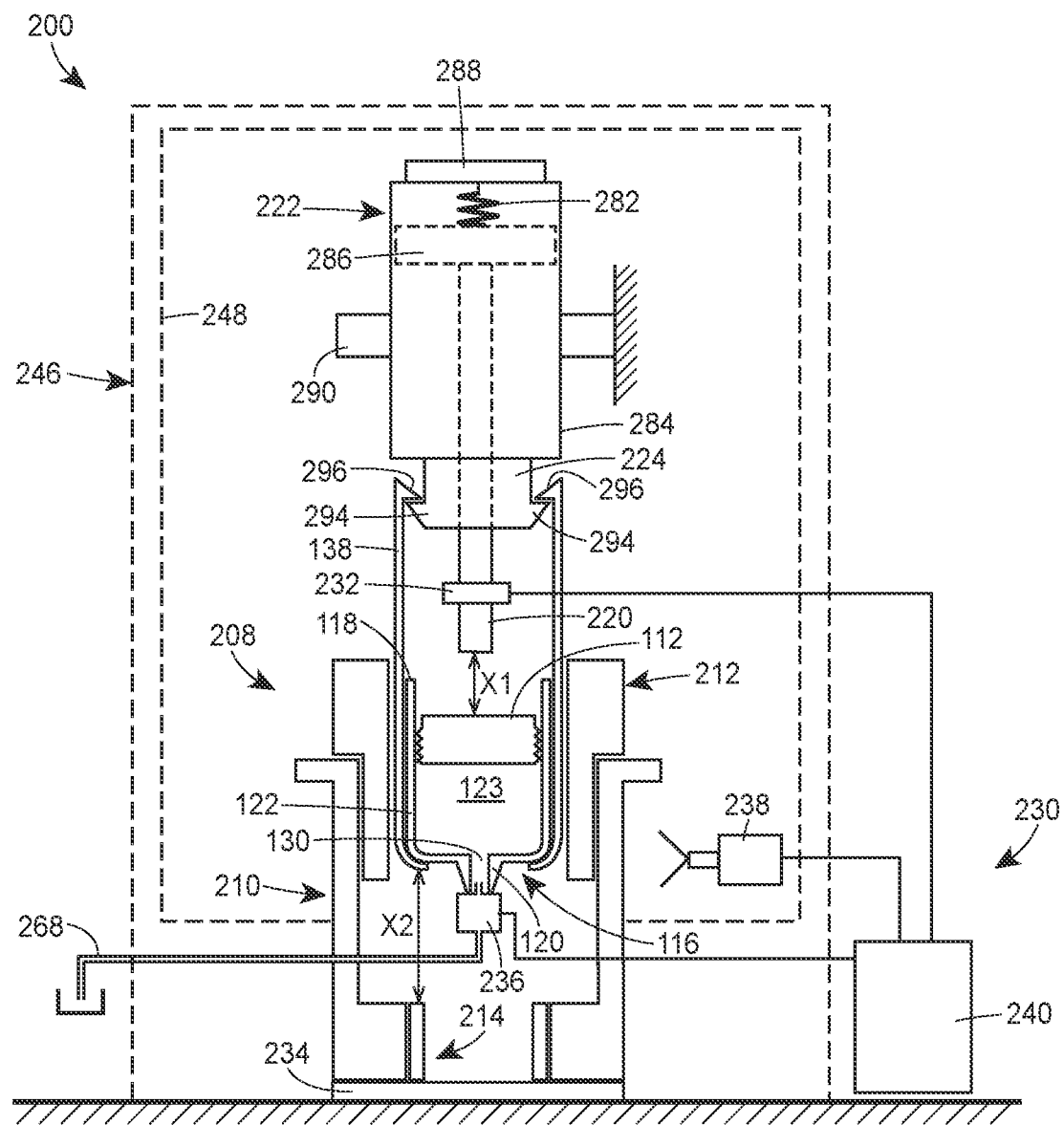
FIG. 2A is a schematic illustration of an impact testing apparatus according to one embodiment of the present disclosure.
Figure 2B:
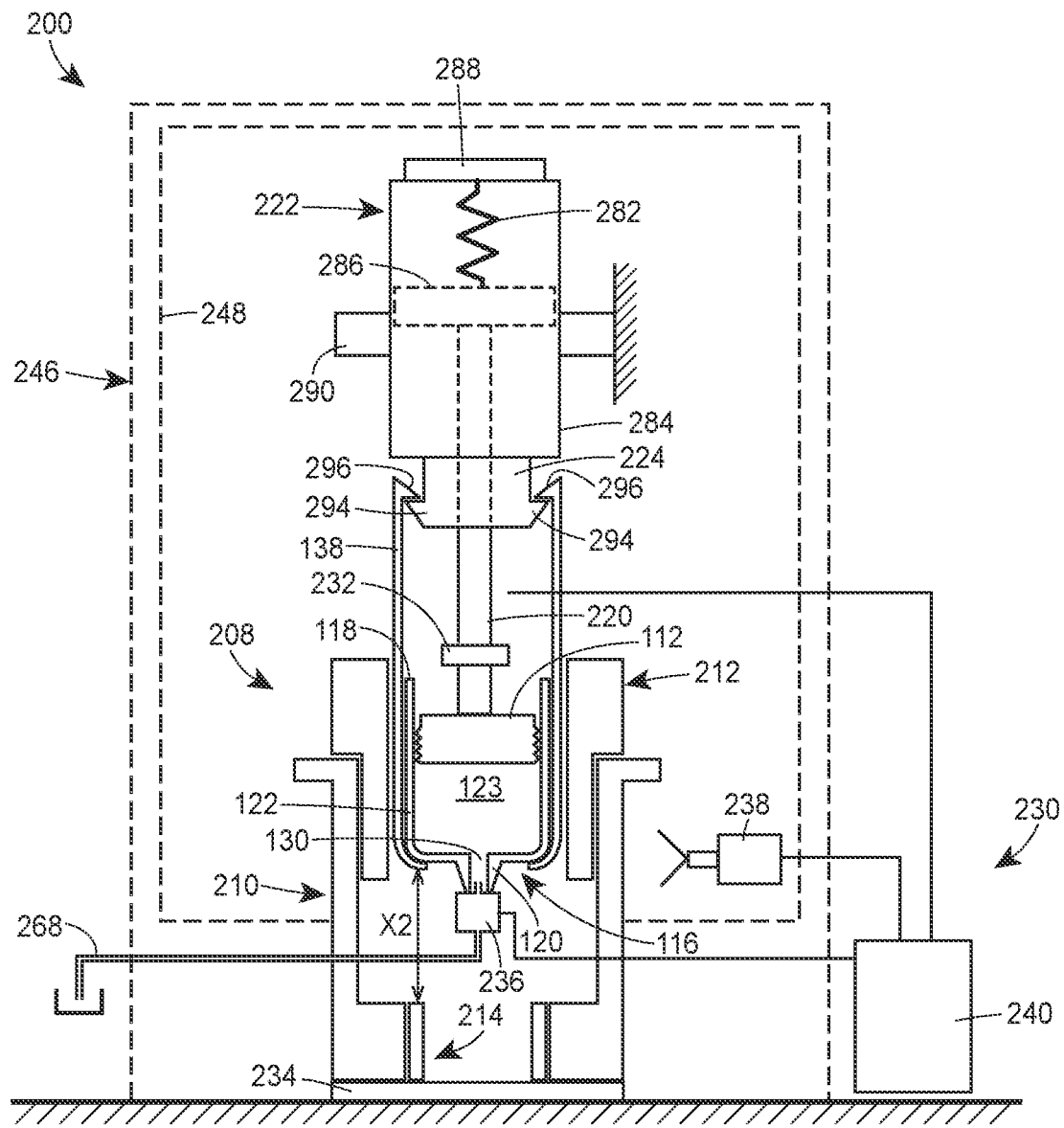
FIG. 2B is a schematic illustration of the impact testing apparatus of FIG. 2A in a first impact state.
Figure 2C:
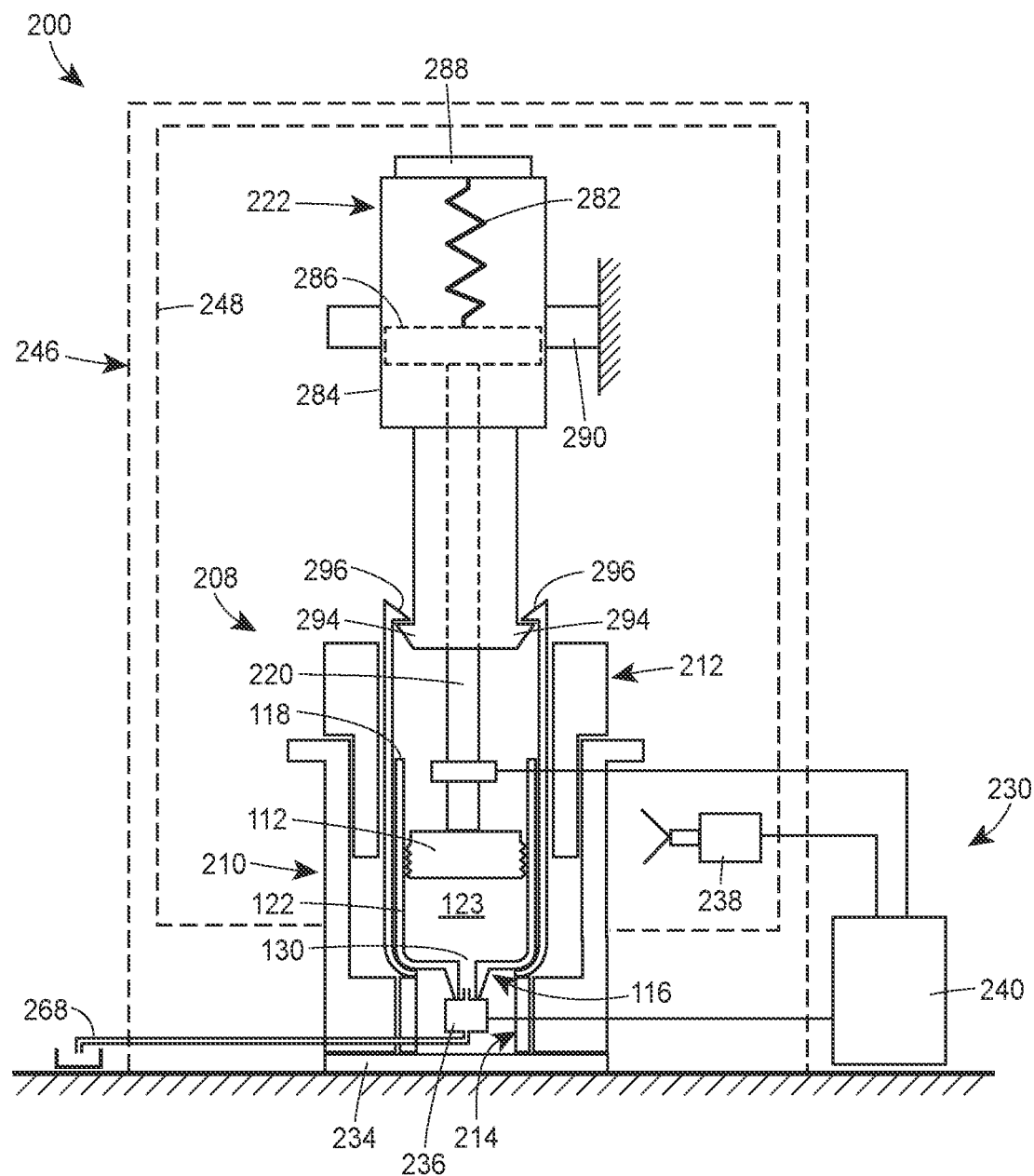
FIG. 2C is a schematic illustration of the impact testing apparatus of FIG. 2A in a second impact state.

Referring to FIG. 2A, the impact testing apparatus 200 may generally include a mounting assembly 208 having an outer shell 210, a guide sleeve 212, and an anvil member 214. The guide sleeve 212 may be configured to receive a specimen to be tested, which in the present case is the syringe 116 encased within the syringe carrier 138. The needle 132 is omitted here, but in other implementations, the needle 132 may be mounted to the distal end 120 of the syringe 116 as shown in FIG. 1B. The anvil member 214 may be positioned below (i.e., distal to) the guide sleeve 212 and define a stop member for preventing further advancement of the syringe carrier 138 during operation. An impactor 220, which may simulate aspects of the plunger rod 110, is positioned above (i.e., proximal to) the syringe 116, and is initially spaced apart from the plunger 112 by a distance X1. The impact testing apparatus 200 may further include an energy source 222 configured to move the impactor 220 in the distal direction to reduce the distance X1 between the impactor 220 and the plunger 112 and cause the impactor 220 to strike and displace the plunger 112 in the distal direction (see FIG. 2B). The impactor 220 striking the plunger 112 may correspond to a first impact event. A second impact event may occur when the syringe carrier 138 strikes the anvil member 214, as illustrated in FIG. 2C, and may simulate the syringe carrier 138 striking an internal wall of an autoinjector. Additionally, the impact testing apparatus 200 may include a retaining member 224 which initially holds the syringe carrier 138 above the anvil member 214 by a distance X2, and which permits the syringe carrier 118 to move relative to the guide sleeve 212 subsequent to the impactor 220 striking the plunger 112. In order to detect characteristics of the first and second impacts, the impact testing apparatus 200 may include a monitoring system 230 comprised of a first load cell 232, a second load cell 234, a pressure sensor 236, and a video camera 238. The monitoring system 230 may further include a computing unit 240 for processing and storing the data collected by the sensors. Additionally, to protect an operator from projectile debris during a test, the impact testing apparatus may include a protective enclosure 246 with an openable door 248.

Each of the foregoing components of the impact testing apparatus 200 and the methods of operating the impacting testing apparatus 200 will now be described in detail.

Figure 3:
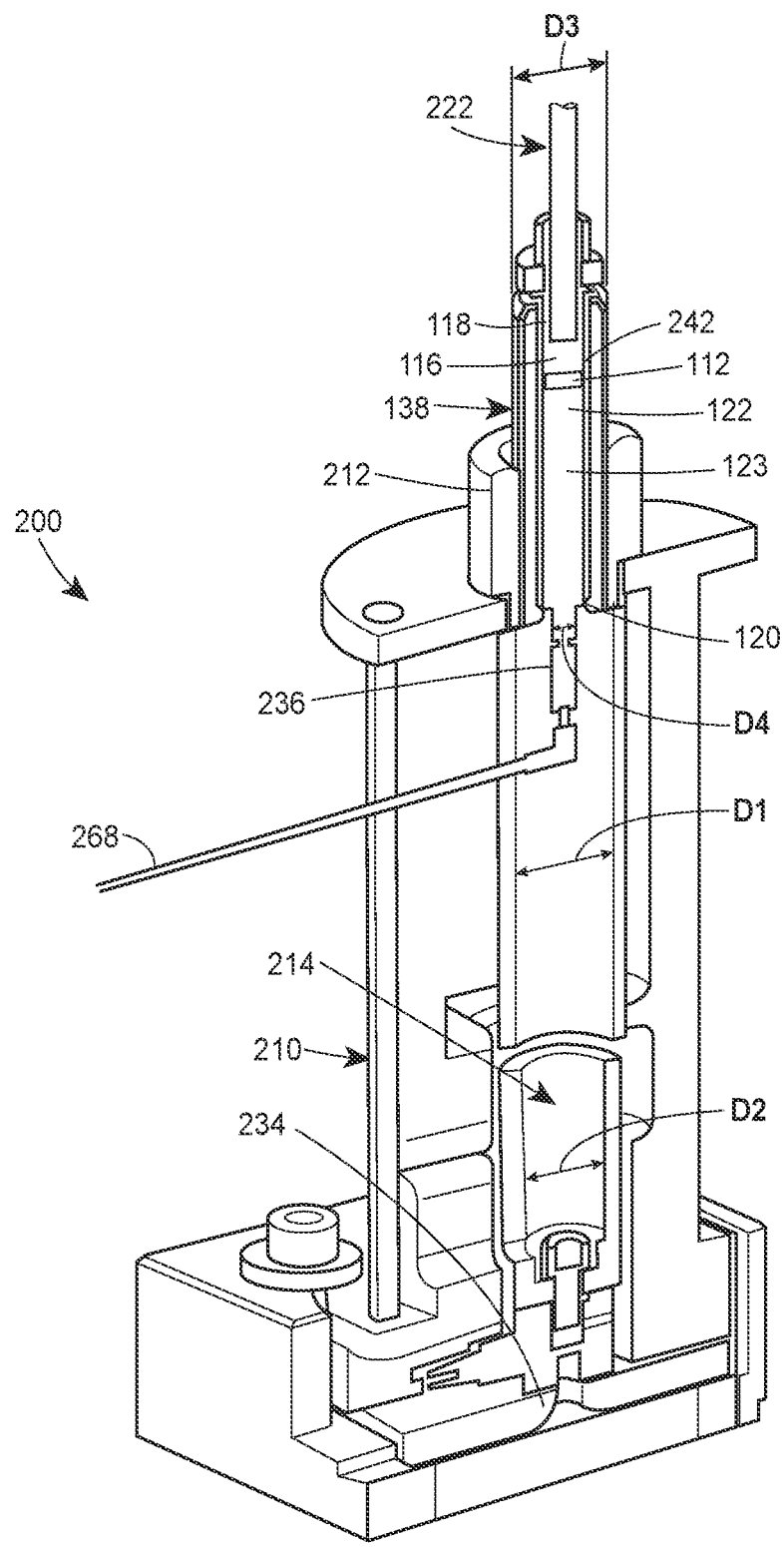
Figure 4A:
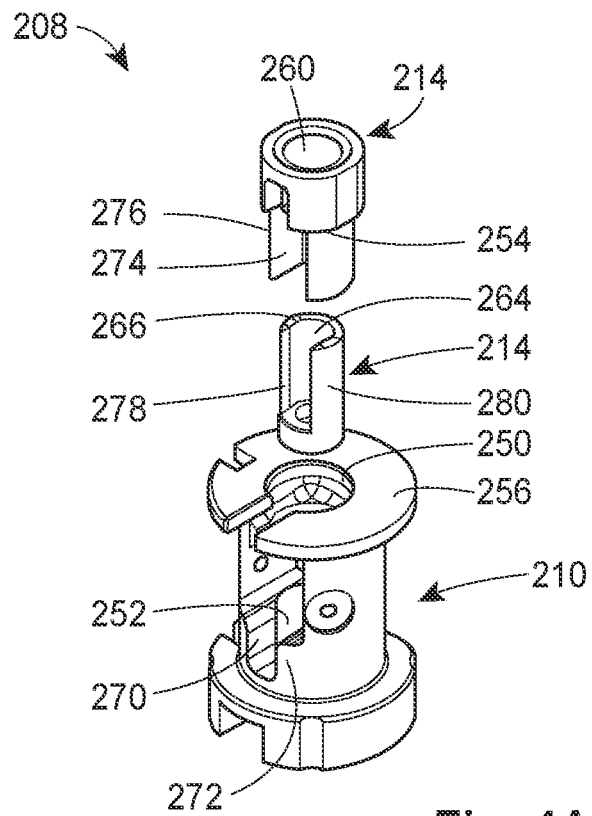
FIG. 4A is an exploded assembly view of the mounting assembly according to one embodiment of the present disclosure.
Figure 4B:
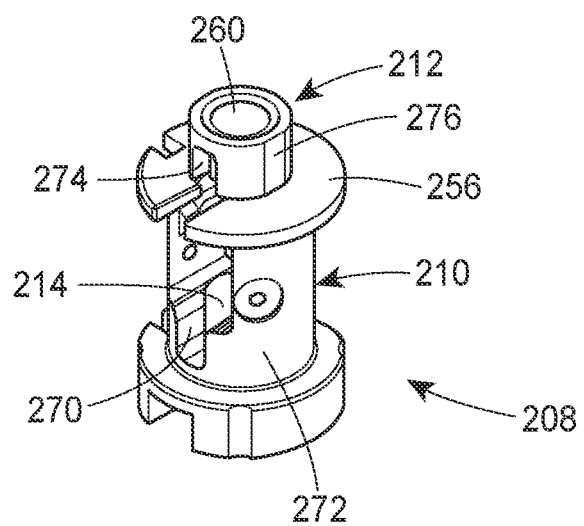
FIG. 4B is an assembled view of the mounting assembly shown in FIG. 4A.

FIGS. 3, 4A, and 4B illustrate various views of an embodiment of the mounting assembly 208. In general, the mounting assembly 208 may facilitate axial movement of the syringe carrier 138 following the first impact event, and provide means for causing the second impact event. The mounting assembly 208 includes the outer shell 210, which may be configured to support and axially align the guide sleeve 212 and the anvil member 214. As shown in FIG. 3, the guide sleeve 212 may be received through an opening 250 in the proximal end of the outer shell 210, whereas the anvil member 214 may be received through an opening 252 in the distal end of the outer shell 210. A proximal end of the guide sleeve 212 may have a larger outer diameter than a distal end of the guide sleeve 212 such that a shoulder 254 is defined between the proximal and distal ends of the guide sleeve 212. The shoulder 254 may rest against a proximal axial end surface 256 of the outer sleeve 210 when the distal end of the guide sleeve 212 is received through the opening 250 in the outer shell 210.

Referring to FIGS. 4A and 4B, the guide sleeve 212 may possess a generally tubular shape and have an axial opening 260 extending between proximal and distal ends of the guide sleeve 212. The axial opening 260 may have an inner diameter D1 which is greater than or equal to an outer diameter D3 of the syringe carrier 138. Accordingly, the syringe carrier 138 may be received through the axial opening 260, as shown in FIGS. 2B, 2C, and 3. During operation of the impact testing apparatus 200, the guide sleeve 212 may permit axial movement of the syringe carrier 138, while preventing or limiting radial movement of the syringe carrier 138.

With continuing reference to FIGS. 4A and 4B, the anvil member 214 may also possess a generally tubular shape and have an axial opening 264 extending between its proximal and distal ends. The axial opening 264 of the anvil member 214 may be axially aligned with the axial opening 260 of the guide sleeve 212 when the anvil member 214 and the guide sleeve 212 are received in their respective openings in the outer shell 210. The axial opening 264 may have an inner diameter D2 which is smaller than the inner diameter D1 of the axial opening 260. Furthermore, the inner diameter D2 may be smaller than the outer diameter D3 of the syringe carrier 138. As such, the syringe carrier 138 may strike a proximal axial end surface 266 of the anvil member 214 after having traversed the distance X2 (see FIG. 2C). Accordingly, the anvil member 214 may define a stop member for the syringe carrier 138.

The inner diameter D2 of the axial opening 264 may be greater than or equal to an outer diameter D4 of the distal end 120 of the syringe 116. Therefore, during operation, the distal end 120 of the syringe 116 may be received through the axial opening 264 of the anvil member 214, which allows the syringe carrier 138 to continue to advance in the distal direction until the syringe carrier 138 strikes the proximal axial end surface 266 of the anvil member 214.

In alternative embodiments, the anvil member 214 may be omitted, and instead the second load cell 234 may be configured as the stop member for the syringe carrier 138. Also, in alternative embodiments, the guide sleeve 212 may be omitted, and instead the outer shell 210 may perform the functions of the guide sleeve 212. Furthermore, in alternative embodiments, the syringe carrier 138 may be omitted, and the syringe 116 may be connected directly to the retaining member 224 and may directly strike the anvil member 214. In further alternative embodiments, the outlet 130 of the syringe 116 may be plugged and the pressure sensor 236 omitted, so that no fluid is discharged from the syringe 116 during a test, or the pressure sensor 236 itself may plug the outlet 130 such that the pressure reading can still be obtained without discharging fluid from the syringe 116.

Still referring to FIGS. 4A and 4B, the outer shell 210, the guide sleeve 212, and the anvil member 214 each may be configured to receive a fluid discharge conduit 268 or other element which protrudes in a radial direction from the distal end 120 of the syringe 116. More particularly, a radial opening 270 may extend through a sidewall 272 of the outer shell 210 and provide radial access to the interior of the outer shell 210. Similarly, a radial opening 274 may extend through a sidewall 276 of the guide sleeve 212 to provide radial access to the axial opening 260 of the guide sleeve 212; and a radial opening 278 may extend through a sidewall 280 of the anvil member 214 to provide radial access to the axial opening 264 of the anvil member 214. When the mounting assembly 208 is assembled (FIG. 4B), the radial openings 270, 274, and 278 may be radially aligned with each other and combine to form a continuous radial access port for the fluid discharge conduit 268 or other radially-extending element. Accordingly, the fluid discharge conduit 268 or other radially-extending element may be free to move in the distal and proximal directions during the operation or setup of the impact testing apparatus 200, without disturbing the mounting assembly 208.

In terms of material, the outer shell 210, the guide sleeve 212, and the anvil member 214 may be made constructed of metal (e.g., stainless steel), plastic, or any other suitably rigid material.

Furthermore, in some embodiments, the axial length of one or more of the outer shell 210, the guide sleeve 212, and the anvil member 214 may be adjustable, such that an operator can adjust the distance X1 and/or the distance X2, for example, to simulate the dimensions of different kinds of drug delivery devices.

As to the energy source 222 and the impactor 220, these components in combination may correspond to the drive mechanism of the impact testing apparatus 200. In some embodiments, the drive mechanism may simulate the operation of a drive mechanism of an actual drug delivery device. For example, the energy source 222 may include a spring having the same spring constant and the same dimensions as the spring 106 of the autoinjector 100, and the impactor 220 may have the same weight and the same dimensions as the plunger rod 110 of the autoinjector 100. Accordingly, the impact testing apparatus 200 may be used to replicate and measure loading conditions which are similar to or the same as those experienced by the autoinjector 100. In alternative embodiments, the drive mechanism may be configured to simulate accelerated loading conditions. For example, the energy source may be comprised of a hydraulic or pneumatic element (e.g., hydraulic or pneumatic cylinder) which operates at much higher loads and/or speeds than the energy source of an actual drug delivery device. By simulating accelerated conditions, the impact testing apparatus 200 may be able to better identify failure points of an actual drug delivery device.

Referring back to FIGS. 2A-2C, the energy source 222 may be powered by a spring 282 (e.g., a coil spring) which is contained within a housing 284 and configured to bias a piston member 286 connected to the impactor 220. Initially, the spring 282 may be retained in an energized stated (e.g., a compressed state) between an interior wall of the housing 284 and the piston member 286, as illustrated in FIG. 2A. The energy source 222 may additionally include an actuator 288 (e.g., a button) which can be pressed or otherwise manually displaced by an operator to release the spring 282, thereby activating the energy source 222. In alternative embodiments, an electromechanical component may be substituted for the actuator 288, such that activation of the energy source 222 can be controlled via a computer (e.g., the computing unit 240). Upon release, the spring 282 may expand axially, thereby pushing the piston member 286 as well as the impactor 220 connected to the piston member 286 in the distal direction. The distal movement of the impactor 220 reduces the distance X1 between the impactor 220 and the plunger 112 until the distal end of the impactor 220 strikes the proximal end of the plunger 112, as shown in FIG. 2B. As the spring 282 continues to expand, the impactor 220 may push the plunger 112 in the distal direction. Friction between the plunger 112 and the interior wall of the barrel 122 may cause the barrel 122 to move together with the plunger 112. As such, the syringe 116 and the syringe carrier 138 (which may be rigidly connected to the syringe 116) may move in the distal direction, thereby reducing the distance X2 between the distal end of the syringe carrier 138 and the proximal end of the anvil member 214. In an alternative embodiment, friction between the plunger 112 and the interior wall of the barrel 122 may not necessarily cause distal movement of the syringe 116 and the syringe carrier 138. Rather, the spring 282 may be operably connected to the retaining member 224, such that axial expansion of the spring 282 moves the retaining member 224 and the syringe carrier 138 (which may be suspended from the retaining member 224) in the distal direction. Subsequently, once the entire distance X2 has been traversed by the syringe carrier 138, the distal end of the syringe carrier 138 may impact the proximal end of the anvil member 214. This may stop further advancement of the syringe carrier 138. However, the impactor 220 may continue to advance in the distal direction under the biasing force of the spring 282. Accordingly, the impactor 220 will move the plunger 112 through the barrel 122 of the syringe 116 to expel the drug inside the barrel 122 through the outlet 130, then through the pressure sensor 236, and then into the discharge conduit 268. The plunger 112 will continue to move in the distal direction until it abuts against the shoulder 126 of the barrel 122 of the syringe 116.

It is apparent from the foregoing discussion that the energy source 222 continuously applies a biasing force to the impactor 220 from the moment of activation through at least when the plunger 112 strikes the shoulder 126 of the barrel 122 of the syringe 116. The energy source 222 does not simply fire the impactor 220 from the starting position shown in FIG. 2A and then rely on the momentum of the impactor 220 to cause the first impact, the second impact, and the movement of the plunger 112.

Figure 6A:
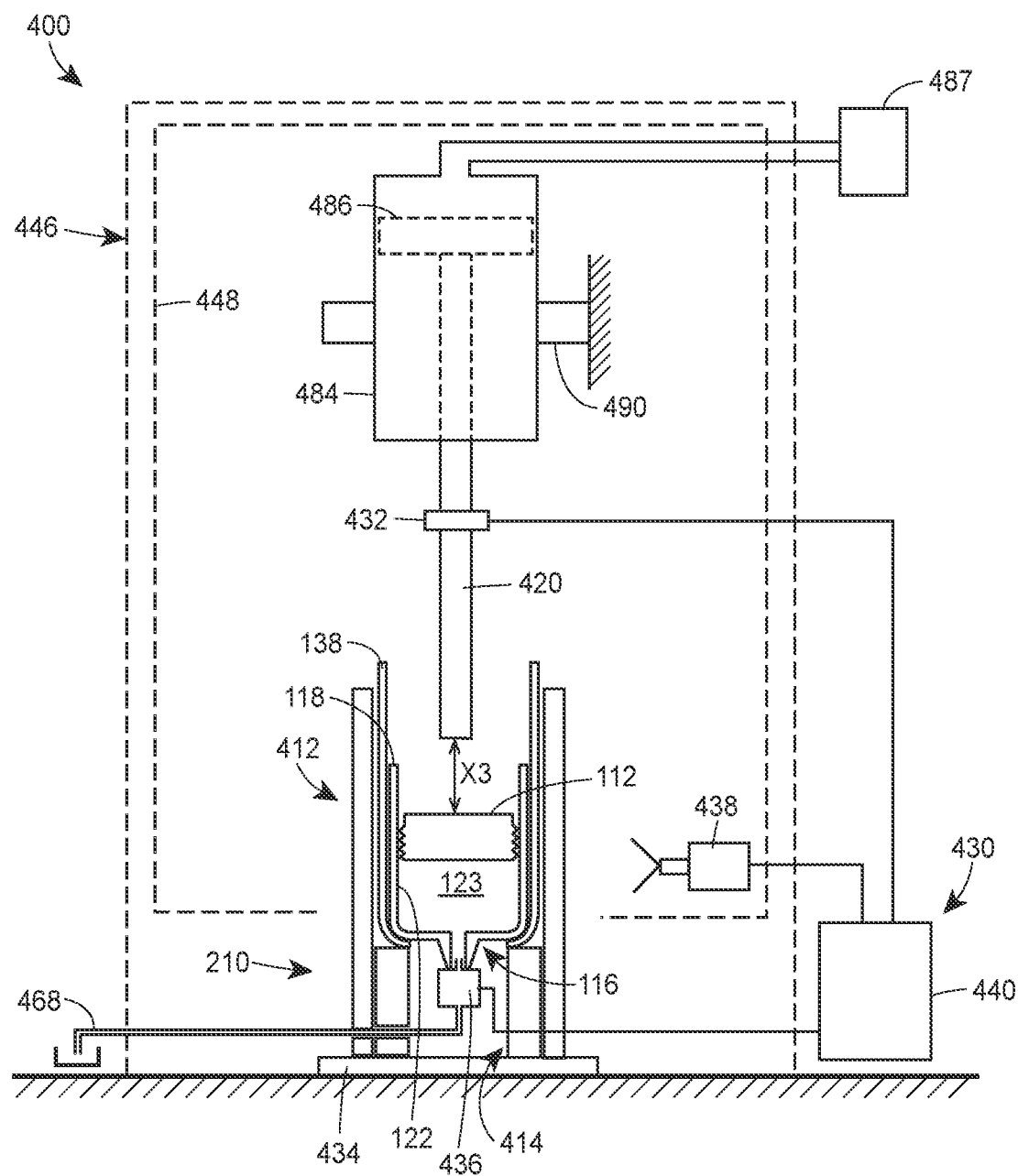
FIG. 6A is a schematic illustration of an impact testing apparatus according to a second embodiment of the present disclosure.
Figure 6B:
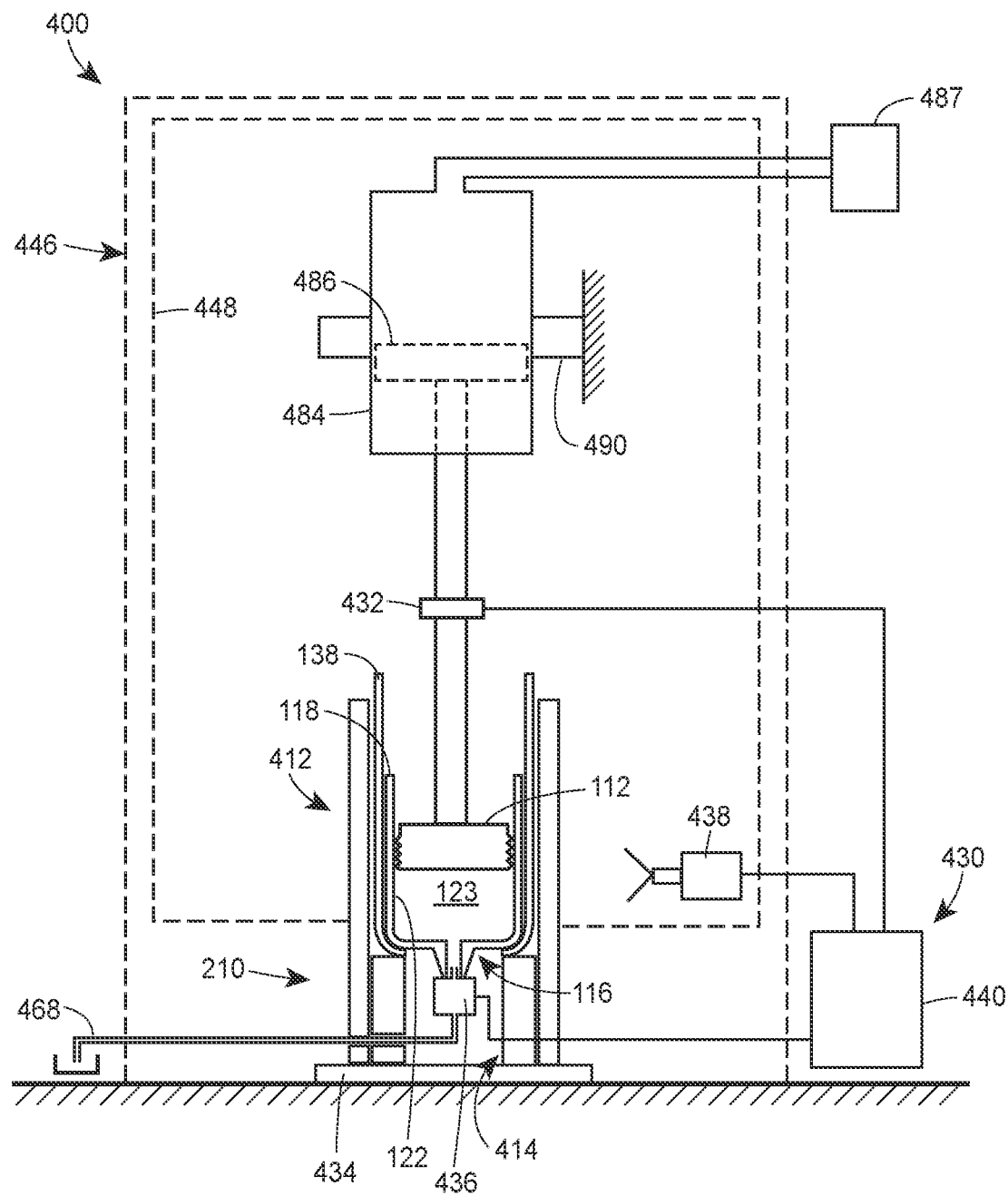
FIG. 6B is a schematic illustration of the impact testing apparatus of FIG. 6A in an impact state.

While the energy source 222 illustrated in FIGS. 2A-2C is powered by a spring, in alternative embodiments, the energy source 222 may be powered by a pneumatic or hydraulic element or source, such as the one used by the impact testing apparatus 400 described below in connection with FIGS. 6A and 6B.

As shown in FIGS. 2A-2C, an adjustable clamp 290 may grip the housing 284 to hold the housing 284 stationary (relative to the Earth). The height of the adjustable clamp 290 may be adjustable, so that an operator can change the distance X1 between the impactor 220 and the plunger 112. Furthermore, the width of an opening defined by the adjustable clamp 290 may be adjustable, such that the adjustable clamp 290 can grip the housings of different energy sources having different geometries and/or sizes.

In general, the impactor 220 simulates the plunger rod (e.g., the plunger rod 110) of a drug delivery device. In some embodiments the impactor 220 may be a solid, or hollow, cylindrical rod. A distal end surface 292 of the impactor 220 may be planar, convex, or even concave, depending on the drug delivery device being simulated.

Still referring to FIGS. 2A-2C, the retaining member 224 may be configured to maintain the position of the syringe 116 relative to the guide sleeve 212 prior to activation of the energy source 222 and may permit the syringe 116 to move relative to the guide sleeve 212 in response to the impactor 220 striking the plunger 112. In order to hold the syringe 116 relative to the guide sleeve 212, the retaining member 224 may be removably connected to the syringe carrier 138, such that the syringe carrier 138 and the syringe 116 are stationarily suspended below the energy source 222 by the retaining member 224. The connection between the retaining member 224 and the syringe carrier 138 may be achieved by a plurality of hooks 294 protruding from the distal end of the retaining member 224 and matingly engaging a plurality of hooks 296 protruding from a proximal end of the syringe carrier 138.

The energy source 222 may include a mechanism (not illustrated) operably connected to the retaining member 224 and which allows the retaining member 224 to move relative to the housing 284 in the distal direction subsequent to the first impact. Accordingly, the retaining member 224 may be configured to move toward the guide sleeve 212 in response to the impactor 220 striking and moving the plunger 112 in the distal direction. Distal movement of the retaining member 224 allows the syringe carrier 138 to move in the distal direction until the syringe carrier 138 strikes the anvil member 214. In an alternative embodiment, the retaining member 224 may be rigidly connected to the energy source 222 such that the retaining member 224 remains stationary relative to the energy source 222 throughout the testing process. In such an embodiment, the syringe carrier 138 may disconnect from the retaining member 224 as a result of the impactor 220 striking and displacing the plunger 112, such that the syringe carrier 138 is then free to move in the distal direction.

Regarding the protective enclosure 246, it may enclose some or all of the elements of the impact testing apparatus 200. At a minimum, the protective enclosure 246 may enclose the mounting assembly 208 and the impactor 220, so that the protective enclosure 246 can contain any projectile debris resulting from the fracture of the syringe 116 and/or the syringe carrier 138 during an impact test. In some embodiments, the protective enclosure 246 may include a rigid frame (not illustrated) that supports a plurality of transparent panels (e.g., Plexiglas panels) allowing an operator or camera to observe operation of the impact testing apparatus 200. One of these transparent panels may be hinged to the frame such it forms the openable door 248.

Figure 5:
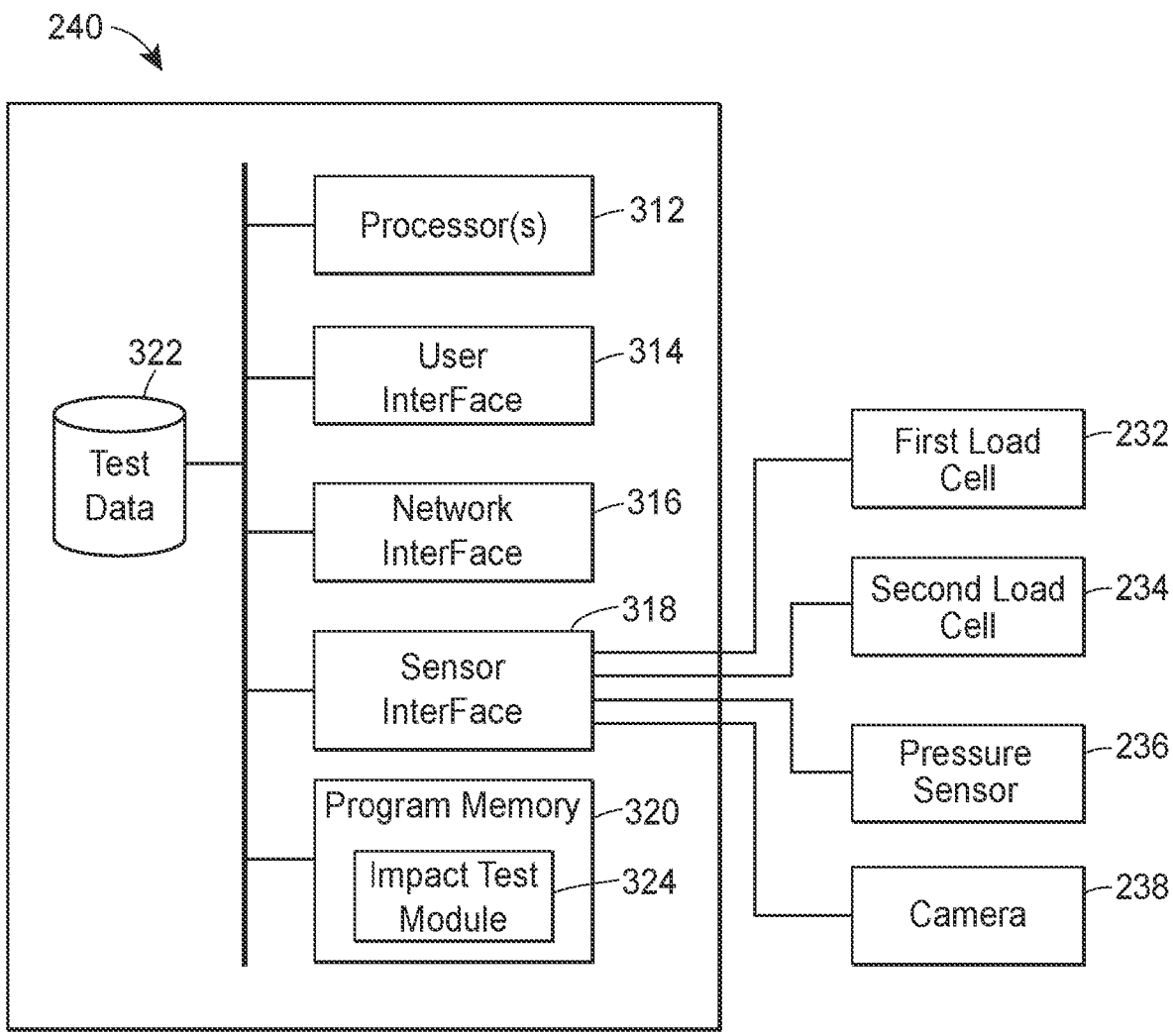
FIG. 5 is a block diagram of a monitoring system according to one embodiment of the present disclosure.

Turning to FIG. 5, illustrated is a block diagram of the monitoring system 230. In general, the monitoring system 230 is configured to measure and analyze various characteristics (e.g., physical properties) of the first and second impacts. As mentioned above, the monitoring system may include various sensors in data communication with the computing unit 240. While the embodiment of the monitoring system 230 depicted in FIG. 5 includes the first load cell 232, the second load cell 234, the pressure sensor 236, and the video camera 238, in other embodiments, one or more of these sensor may be omitted, and/or additional sensors may be included. For example, stress and/or strain gauges could be mounted on the syringe 116, vibration or accelerometer sensors mounted on the syringe 116, and/or temperature sensors could be mounted on the syringe 116.

The first and second load cells 232 and 234 each may be include a transducer that outputs an electrical signal whose magnitude is proportional to the force being measured. Various types of load cells can be used for first and second loads cells 232 and 234 including, but not limited to, strain gauge load cells and/or piezoelectric load cells. The electrical signal outputted by the first load cell 232 to the computing unit 240 is referred to as a first force signal, and the electrical signal outputted by the second load cell 234 to the computing unit 240 is referred to as a second force signal. As shown in FIG. 2A, the first load cell 232 may be connected directly to the impactor 220 and the second load cell 234 may be connected below and support the anvil member 214. Because the impactor 220 is involved with both the first and second impacts, the first force signal may be used to measure forces generated by both the first and second impacts. The second force signal may only be used to measure forces generated by the second impact.

The pressure sensor 236 may include a transducer that outputs an electrical signal whose magnitude is proportional to the pressure of the fluid (e.g., the drug) expelled from the syringe 116 by the plunger 112. As shown in FIG. 3, the pressure sensor 236 may be in fluid communication with the outlet 130 of the syringe 116 and in fluid communication with the fluid discharge conduit 268. So configured, fluid discharged from the syringe 116 during an impact test may flow through the pressure sensor 236.

The video camera 238 may be mounted so that its field of view includes one or both of the first and second impacts. A video signal outputted by the video camera 238 may be analyzed by the computing unit 240 to determine the velocity of the impactor 220, the plunger 112, and/or the barrel 122, or any other moving component, before, after, and/or during the first impact and/or the second impact.

Referring to FIG. 5, the computing unit 240 may include a desktop computer, a portable computer, a smartphone, a tablet computer, and/or a server. In at least one embodiment, the computing unit 240 may include one or more processors 312 (e.g., CPUs), a user interface 314 (e.g., a touchscreen, a monitor, a keyboard, etc.), a network interface 316 configured for wired and/or wireless communications with a network, a sensor interface 318 configured for wired and/or wireless communications with the above-described sensors, a non-transitory computer-readable program memory 320, a test data storage 322, each of which may be interconnected by a communication link such as a digital bus. The program memory 320 can include persistent (e.g., a hard disk) as well as non-persistent (e.g., RAM) components. The test data storage 322 can be implemented in a local or remote memory in accordance with any suitable data storage techniques (e.g., as a relational database).

An impact test module 324 may be stored in the program memory 320 as a set of instructions executable on the one or more processors 312. The impact test module 324 may receive and process one or more of the first force signal, the second force signal, the pressure signal, the video signal, and/or other signals from other sensors to generate data representative of the one or more impacts (e.g., the first and/or second impact) caused by the operation of the impact testing apparatus 200. In some embodiments, the impact test module 324 may generate graphs, charts, infographics, tables, and/or other visual representations of the data, and display those visual representations via a screen included in the user interface 314. Such visual representations may include, but are not limited to: (a) a force vs. time graph representative of the first impact and/or the second impact; (b) a pressure vs. time graph representative of the first impact and/or the second impact; (c) a pressure vs. force graph representative of the first impact and/or the second impact; (d) force vs. velocity graph representative of the first impact and/or the second impact; and/or (e) pressure vs. velocity graph representative of the first impact and/or the second impact. Furthermore, in some embodiments, the impact test module 324 may store the data it generates in the test data storage 322.

Performing an impact test with the impact testing apparatus 200 may involve one or more of the following steps. Initially, the barrel 120 of the syringe 116 may be filled with a fluid (e.g., a drug or a fluid simulating a drug) and the plunger 112 may be inserted into the proximal end of the barrel 120. In the case where the syringe 116 being tested is a pre-filled syringe, this step may be performed by a drug manufacturer. Next, the syringe 116 may be inserted into and rigidly connected to the syringe carrier 138. In some embodiments, this step may be performed before the barrel 120 is filled with the fluid. Next, the syringe carrier 138 may be inserted into the axial opening 260 of the guide sleeve 212, so that the plunger 112 is axially aligned with the impactor 220. Subsequently, the proximal end syringe carrier 138 may be lifted by the operator in the proximal direction, and connected to the retaining member 224, for example, by matingly engaging the hooks 294 and 296. As a result, the impactor 220 may be spaced apart from the plunger by the distance X1 and the syringe carrier 138 may be spaced apart from the anvil member 214 by the distance X2. Next, the operator may press the actuator 288 to activate the energy source 222. In the manner described above, the energy source 222 may then cause the impactor 220 to strike and move the plunger 112 in the distal direction, which in turn may cause the syringe carrier 138 to move in the distal direction and strike the anvil member 214. During this process, the first load cell 232, the second load cell 234, the pressure sensor 236, and/or the video camera 238 may output respective signals to the computing unit 240 which, in turn, generates data representative of the first and/or second impacts, as described above.

While the impact testing apparatus 200 described above simulates and measures two separate impact events, the scope of the present disclosure is not limited to this configuration. Rather, alternative embodiments, such as the impact testing apparatus 400 illustrated in FIGS. 6A and 6B, may be configured to simulate and measure a single impact event. Elements of the impact testing apparatus 400 which are similar to the impact testing apparatus 200 are designated by the same reference numeral, incremented by 200. A description of many of these elements is abbreviated or even eliminated in the interest of brevity.

In general, the impact testing apparatus 400 may be configured to simulate and measure the first impact (i.e., the impactor 420 striking the plunger 112). The impact testing apparatus 400 may include a mounting assembly 408 including a guide sleeve 412 and an anvil member 414. The impact testing apparatus 400 may not include an element corresponding to the outer shell 210. The guide sleeve 412 may be configured to receive the specimen to be tested, which in the present case is the syringe 116. The needle 132 is omitted here, but in other implementations, the needle 132 may be mounted to the distal end 120 of the syringe 116. The anvil member 414 may be disposed within the guide sleeve 412 and define a stop member for preventing further advancement of the syringe carrier 138 during operation. An impactor 420, which may simulate aspects of the plunger rod 110, is positioned above (i.e., proximal to) the syringe 116, and is initially spaced apart from the plunger 112 by a distance X3 (see FIG. 6A). The impact testing apparatus 200 may further include an energy source 422 configured to move the impactor 420 in the distal direction to reduce the distance X3 between the impactor 420 and the plunger 212 and cause the impactor 420 to strike and displace the plunger 112 in the distal direction (see FIG. 6B). The impactor 420 striking the plunger 112 may correspond to a first and only impact event. In order to detect characteristics of this impact, the impact testing apparatus 400 may include a monitoring system 430 comprised of a load cell 432, a second load cell 434, a pressure sensor 436, and a video camera 438. The monitoring system 430 may further include a computing unit 440 for processing and storing the data collected by the sensors. Additionally, to protect an operator from projectile debris during a test, the impact testing apparatus may include a protective enclosure 446 with an openable door 448.

Unlike the testing apparatus 200, the anvil member 414 of the testing apparatus 400 may support the syringe carrier 138 prior to the impactor 420 striking the plunger 112. Furthermore, the anvil member 414 may be configured to hold the syringe carrier 138 stationary relative to the impactor 420 when the impactor 420 strikes the plunger 112 and also while the impactor 420 drives the plunger 112 in the distal direction. Furthermore, unlike the testing apparatus 200, the energy source 422 may not be powered by a spring. Rather, as shown in FIGS. 6A and 6B, the energy source 422 may be powered by a pneumatic or hydraulic cylinder 482 including a piston member 486 connected to the impactor 420. The pneumatic or hydraulic cylinder 482 may be controllably supplied with a pressurized gas of fluid from a pump 487. The pneumatic or hydraulic cylinder 482 may be configured to operate the impactor 420 at much greater velocities and/or forces than the energy source of a drug delivery device. Accordingly, the hydraulic cylinder 482 may facilitate testing under acceleration conditions. In alternative embodiments, the energy source 422 may be powered by a spring similar to the energy source 222.

In alternative embodiments, the anvil member 414 may be omitted, and instead, the second load cell 434 may be configured as the support for the syringe 116 and/or syringe carrier 138. Furthermore, in alternative embodiments, the syringe carrier 138 may be omitted, and the syringe 116 may be supported directly by the anvil member 414. In still further alternative embodiments, the outlet 130 of the syringe 116 may be plugged and the pressure sensor 436 omitted, so that no fluid is discharged from the syringe 116 during a test.

Performing an impact test with the impact testing apparatus 400 may involve a similar set of steps as those described above in connection with the impact testing apparatus 200. However, instead of connecting the syringe carrier 138 to a retaining member, the syringe carrier 138 may be disposed against and supported by the anvil member 414 prior to activation of the energy source 422.

Drug Information

As mentioned above, the syringe or other container being tested may be filled with a drug. This drug may be any one or combination of the drugs listed below, with the caveat that the following list should neither be considered to be all inclusive nor limiting.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormone (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18G2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, Al2, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasm id 15H12/19D12 HCA ($\gamma$4), deposited at the ATCC under number PTA-5214, and a light chain encoded by a polynucleotide in plasm id 15H12/19D12 LCF ($\kappa$), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-+4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion®

(visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol, 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

While the present disclosure has been described in connection with various embodiments, it will be understood that the present disclosure is capable of further modifications. The present disclosure is intended to cover any variations, uses, or adaptations of the disclosed subject matter following, in general, the principles of the present disclosure, and including such departures from the present disclosure as, within the known and customary practice within the art to which the present disclosure pertains.

It is noted that the construction and arrangement of the impact testing apparatus as shown in the various exemplary embodiments is illustrative only. Although only a few embodiments of the subject matter at issue have been described in detail in the present disclosure, those skilled in the art who review the present disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, and vice versa. Also, the position of elements may be reversed or otherwise varied, and the nature or number of discrete elements or positions may be altered or varied. Accordingly, all such modifications are intended to be included within the scope of the present disclosure as defined in the appended claims. Furthermore, the order or sequence of any process or method steps may be varied or re-sequenced according to alternative embodiments. Other substitutions, modifications, changes and omissions may be made in the design, operating conditions and arrangement of the various exemplary embodiments without departing from the scope of the present disclosure.

What is claimed is:

1. A testing apparatus for simulating operation of a drug delivery device having a container containing a fluid and a plunger, the plunger having a distally facing end surface and a proximally facing end surface each being disposed within the container, the testing apparatus comprising:
   a guide sleeve configured to receive a syringe, the syringe having a proximal end, a distal end, and a plunger;
   an impactor configured to simulate a plunger rod of the drug delivery device, wherein at least a distal end of the impactor is configured to fit within the container of the drug delivery device;
   an energy source configured to reduce a distance between the impactor and the plunger such that the distal end of the impactor contacts the proximally facing end surface of the plunger; and
   a monitoring system configured to measure at least one characteristic of at least one impact caused by the impactor.

2. The testing apparatus of claim 1, further comprising a retaining member configured to maintain a position of the syringe relative to the guide sleeve prior to activation of the energy source and permit the syringe to move relative to the guide sleeve in response to the impactor contacting the plunger.

3. The testing apparatus of claim 2, comprising a first impact state, where the impactor initially contacts the plunger and the retaining member occupies a first position, and a second impact state, where the impactor causes the syringe or a carrier holding the syringe to contact an anvil member and the retaining member occupies a second position.

4. The testing apparatus of claim 2, the retaining member being configured to move toward the guide sleeve in response to the impactor contacting and moving the plunger.

5. The testing apparatus of claim 1, further comprising an anvil member having a first axial opening aligned with a second axial opening of the guide sleeve, the first axial opening of the anvil member having a smaller inner diameter than the second axial opening of the guide sleeve.

6. The testing apparatus of claim 5, further comprising a first radial opening extending through a sidewall of the anvil member, a second radial opening extending through a sidewall of the guide sleeve, the first and second radial openings being aligned with each other to provide access to the first and second axial openings through the respective sidewalls of the anvil member and the guide sleeve.

7. The testing apparatus of claim 1, the monitoring system comprising a sensor and a computing unit to receive and process a pressure signal and/or a force signal output by the sensor.

8. The testing apparatus of claim 7, the monitoring system comprising a digital camera configured to capture video of the one or more impacts caused by the impactor and output a video signal to the computing unit, wherein the computing unit calculates one or more velocities based on the video signal.

9. The testing apparatus of claim 1, the monitoring system comprising a load cell disposed distal to the guide sleeve.

10. The testing apparatus of claim 1, the monitoring system comprising a first load cell and a second load cell, the first load cell being connected to and moveable with the impactor and configured to output a first force signal, the second load cell being mounted stationarily relative to the impactor and configured to output a second force signal representative.

11. The testing apparatus of claim 10, the first force signal being representative of at least a first impact caused by the impactor, and the second force signal being representative of at least a second impact caused by the impactor.

12. The testing apparatus of claim 1, comprising a protective enclosure having an openable door, at least the guide sleeve and the impactor being disposed within the protective enclosure.

13. The testing apparatus of claim 1, the energy source comprising a hydraulic or pneumatic element configured to drive the impactor.

14. The testing apparatus of claim 1, the energy source comprising a spring configured to drive the impactor.

15. The testing apparatus of claim 14, the energy source comprising a manually operable actuator for releasing the spring.

16. The testing apparatus of claim 1, comprising an adjustable clamp for mounting the energy source.

17. The testing apparatus of claim 1, the monitoring system comprising a pressure sensor configured to output a pressure signal representative of a pressure of a fluid expelled from the syringe.

18. The testing apparatus of claim 1, the monitoring system comprising a load cell configured to output a force signal representative of the at least one impact caused by the impactor.

19. A testing apparatus for simulating operation of a drug delivery device, the testing apparatus comprising:
   a guide sleeve configured to receive a syringe, the syringe having a proximal end, a distal end, and a plunger;
   an impactor configured to simulate a plunger rod of the drug delivery device;
   an energy source configured to reduce a distance between the impactor and the plunger such that the impactor contacts the plunger;
   a monitoring system configured to measure at least one characteristic of at least one impact caused by the impactor;

a retaining member configured to maintain a position of the syringe relative to the guide sleeve prior to activation of the energy source and permit the syringe to move relative to the guide sleeve in response to the impactor contacting the plunger; and a first impact state, where the impactor initially contacts the plunger and the retaining member occupies a first position, and a second impact state, where the impactor causes the syringe or a carrier holding the syringe to contact an anvil member and the retaining member occupies a second position.

20. A testing apparatus for simulating operation of a drug delivery device, the testing apparatus comprising:

a guide sleeve configured to receive a syringe, the syringe having a proximal end, a distal end, and a plunger;

an impactor configured to simulate a plunger rod of the drug delivery device;

an energy source configured to reduce a distance between the impactor and the plunger such that the impactor contacts the plunger; and a monitoring system configured to measure at least one characteristic of at least one impact caused by the impactor, the monitoring system comprising a first load cell and a second load cell, the first load cell being connected to and moveable with the impactor and configured to output a first force signal, the second load cell being mounted stationarily relative to the impactor and configured to output a second force signal representative.

21. A testing apparatus for simulating operation of a drug delivery device, the testing apparatus comprising:

a guide sleeve configured to receive a syringe, the syringe having a proximal end, a distal end, and a plunger;

an impactor configured to simulate a plunger rod of the drug delivery device;

an energy source configured to reduce a distance between the impactor and the plunger such that the impactor contacts the plunger;

a monitoring system configured to measure at least one characteristic of at least one impact caused by the impactor;

an anvil member having a first axial opening aligned with a second axial opening of the guide sleeve, the first axial opening of the anvil member having a smaller inner diameter than the second axial opening of the guide sleeve; and a first radial opening extending through a sidewall of the anvil member, a second radial opening extending through a sidewall of the guide sleeve, the first and second radial openings being aligned with each other to provide access to the first and second axial openings through the respective sidewalls of the anvil member and the guide sleeve.

* * * * *